United States Patent
Serban et al.

(10) Patent No.: US 10,647,637 B2
(45) Date of Patent: May 12, 2020

(54) DEHYDROGENATION PROCESS

(71) Applicant: UOP LLC, Des Plaines, IL (US)

(72) Inventors: Manuela Serban, Northbrook, IL (US); Michael J. Vetter, Schaumburg, IL (US); Gregory J. Nedohin, Des Plaines, IL (US); Clayton C. Sadler, Arlington Heights, IL (US)

( * ) Notice: Subject to any disclaimer, the term of this patent is extended or adjusted under 35 U.S.C. 154(b) by 0 days.

(21) Appl. No.: 16/178,413

(22) Filed: Nov. 1, 2018

(65) Prior Publication Data

US 2019/0127298 A1    May 2, 2019

Related U.S. Application Data

(60) Provisional application No. 62/580,794, filed on Nov. 2, 2017, provisional application No. 62/580,768, filed on Nov. 2, 2017.

(51) Int. Cl.
*C07C 5/333* (2006.01)
*B01J 35/02* (2006.01)
*B01J 8/02* (2006.01)
*C07C 5/48* (2006.01)
*C07C 7/04* (2006.01)
(Continued)

(52) U.S. Cl.
CPC ............ *C07C 5/3337* (2013.01); *B01J 8/02* (2013.01); *B01J 8/0214* (2013.01); *B01J 19/0013* (2013.01); *B01J 35/026* (2013.01); *C07C 5/48* (2013.01); *C07C 7/04* (2013.01); *B01J 2208/00017* (2013.01); *B01J 2208/00539* (2013.01); *B01J 2208/00805* (2013.01); *B01J 2208/00884* (2013.01);
(Continued)

(58) Field of Classification Search
CPC ..... C07C 5/3337; C07C 7/04; C07C 2523/42; C07C 11/06; C07C 5/48; C07C 2523/40; C07C 2523/14; C07C 2523/08; C07C 2523/02; C07C 2521/04; B01J 19/0013; B01J 8/02; B01J 35/026; B01J 2219/00195; B01J 2219/00051; B01J 2208/00884; B01J 2208/00805; B01J 2208/024; B01J 2208/00539; B01J 2208/00017; B01J 8/0214
See application file for complete search history.

(56) References Cited

U.S. PATENT DOCUMENTS 3,670,044 A    6/1972   Drehman et al.
4,418,237 A    11/1983  Imai
(Continued)

FOREIGN PATENT DOCUMENTS

CN    1201715      12/1998
CN    105214657    1/2016
(Continued)

OTHER PUBLICATIONS

Johnson Screens, Internals for Radial Flow Reactors, 2006 Johnson Screens HPI-RF01.

*Primary Examiner* — Ali Z Fadhel

(57) ABSTRACT

Large pill dehydrogenation catalysts and large screens slot width are combined in dehydrogenation units to reduce the pressure drop across the catalyst bed and reactor screens compared to conventional screen and catalyst size combinations. The catalyst has an average pill diameter in the range of 1.6 mm to 3.0 mm, and the slot width of the screen is in the range of about 30% to about 60% of the pill diameter.

20 Claims, 3 Drawing Sheets

(51) Int. Cl.
*B01J 19/00* (2006.01)
*C07C 11/06* (2006.01)

(52) U.S. Cl.
CPC ............... *B01J 2208/024* (2013.01); *B01J 2219/00051* (2013.01); *B01J 2219/00195* (2013.01); *C07C 11/06* (2013.01); *C07C 2521/04* (2013.01); *C07C 2523/02* (2013.01); *C07C 2523/08* (2013.01); *C07C 2523/14* (2013.01); *C07C 2523/40* (2013.01); *C07C 2523/42* (2013.01)

(56) References Cited

U.S. PATENT DOCUMENTS

| | | | |
|---|---|---|---|
| 4,613,715 A | 9/1986 | Haskell | |
| 4,788,371 A | 11/1988 | Imai et al. | |
| 4,914,075 A | 4/1990 | Bricker et al. | |
| 5,324,880 A | 6/1994 | Dyroff | |
| 6,417,135 B1 * | 7/2002 | Dyroff | B01J 23/40 502/20 |
| 6,756,340 B2 | 6/2004 | Voskoboynikov et al. | |
| 6,969,496 B2 | 11/2005 | Vetter | |
| 8,309,782 B2 | 11/2012 | Le Peltier et al. | |
| 8,895,797 B2 | 11/2014 | Myers et al. | |
| 2005/0033101 A1 | 2/2005 | Voskoboynikov et al. | |
| 2013/0340229 A1 * | 12/2013 | Vetter | B01J 8/008 29/428 |
| 2015/0111720 A1 | 4/2015 | Vaidya et al. | |

FOREIGN PATENT DOCUMENTS

| | | |
|---|---|---|
| WO | 2015084041 | 6/2015 |
| WO | 2016005896 | 1/2016 |

\* cited by examiner

DEHYDROGENATION PROCESS

This application claims the benefit of U.S. Provisional Patent Application Ser. No. 62/580,768 filed Nov. 2, 2017, and U.S. Provisional Patent Application Ser. No. 62/580,794 filed Nov. 2, 2017, each of which is hereby incorporated by reference in its entirety.

BACKGROUND

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. One example is the dehydrogenation of propane to propylene which is one of the most important raw materials in the petrochemical industry. Another example of this process is the dehydrogenation of isobutane to produce isobutylene which can be polymerized to provide tackifying agents for adhesives, viscosity-index additives for motor oils, and impact-resistant and antioxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 (Imai et al), U.S. Pat. No. 4,438,288 (Imai et al), and U.S. Pat. No. 6,756,340 (Voskoboynikov et al.) discuss a dehydrogenation process and catalyst for use therein.

The dehydrogenation of hydrocarbons process utilizes radial flow reactors constructed such that the reactor has an annular structure and annular distribution and collection devices. The devices for distribution and collection incorporate some type of screened surface. The screened surface is for holding catalyst beds in place and for aiding in the distribution of pressure over the surface of the reactor to facilitate radial flow through the reactor bed. The screen can be a mesh, either wire or other material, or a punched plate. For a moving bed, the screen or mesh provides a barrier to prevent the loss of solid catalyst particles while allowing fluid to flow through the bed. Solid catalyst particles are added at the top, flow through the apparatus, and are removed at the bottom, while passing through a screened-in enclosure that permits the flow of fluid over the catalyst. For example, the screens are described in U.S. Pat. Nos. 9,266,079 and 9,433,909 (Vetter et al.).

The reactor 10 in FIG. 1, includes a reactor shell 20, one partition in the form of a centerpipe 30, an outer partition in the form of screened partition 40, and a solid particle, or catalyst, bed 50. The reactor 10 can be configured so that fluid enters the reactor 10 through an inlet 32 at the bottom of the reactor and travels upwardly through the centerpipe 30 in the direction indicated by arrow 11. As the fluid flows upwardly, portions of the fluid are directed radially through the centerpipe into the catalyst bed 50 where the fluid contacts the catalyst and reacts to form a product stream. The product stream flows radially outwardly through the outer screened partition 40 and into the annular space 14 between the screened partition 40 and the reactor shell 20. The product stream is collected in the annular space 14 and passes through a reactor outlet 12.

The reactor, according to FIG. 2, may be configured to have an opposite flow pattern such that fluid enters through an inlet 13 and enters the annular space 14 between the reactor shell 20 and the outer screened partition 40 and flows radially inwardly through the catalyst bed 50 where it contacts the catalyst and reacts to form a product stream. The product stream flows radially inwardly through the center pipe 30 where it is collected in the centerpipe and exits through the outlet 33.

If the reactor includes a radial outward flow configuration like that shown in FIG. 1, the centerpipe 30 includes an outer catalyst-side profile wire screen and an inner fluid-side perforated plate. The outer partition may also include an inner catalyst-side profile wire screen and/or an outer fluid-side perforated plate. Alternatively, where the reactor includes the radially inward flow configuration of FIG. 2, the outer partition 40 includes an inner catalyst-side profile wire screen and an outer fluid-side perforated plate. The centerpipe 30 may also include an outer catalyst-side profile wire screen and/or inner fluid-side perforated plate.

The centerpipe 30 and partition 40 must perform the duty of preventing the passage of solid catalyst particles and allowing the passage of fluid, while providing structural strength to hold the catalyst against the pressure of the weight of the solid particles.

In radial bed reactors with substantially continuous catalyst circulation, the forces exerted on the catalyst bed by the gas flow must be considered to ensure uninhibited catalyst movement. The direction of the gas flow through the catalyst bed is generally cross current to the desired direction of the catalyst movement in the active bed. Under the right conditions, excessive gas velocities may impact catalyst movement either by holding up solids flow, i.e., "pinning", or creating a void space, i.e., "void blowing". Both are undesired effects which will adversely impact the flow of catalyst. These two undesirable effects are exacerbated by increasing the velocity of gas or throughput. Increasing the velocity or throughput is desirable because it permits an increase in capacity with only minor operating changes to the existing equipment. In addition, as the velocity of gas or throughput are increased, the pressure drop through the catalyst bed is also increased. The dehydrogenation of hydrocarbons is an equilibrium reaction, thermodynamically favored by high temperature and low pressure. Any increase in pressure causes a decrease in conversion and is undesirable.

Accordingly, there is a need for a process which reduces the pressure drop through the catalyst bed and increases the capacity of the reactors.

SUMMARY AND DETAILED DESCRIPTION

Figure 1:
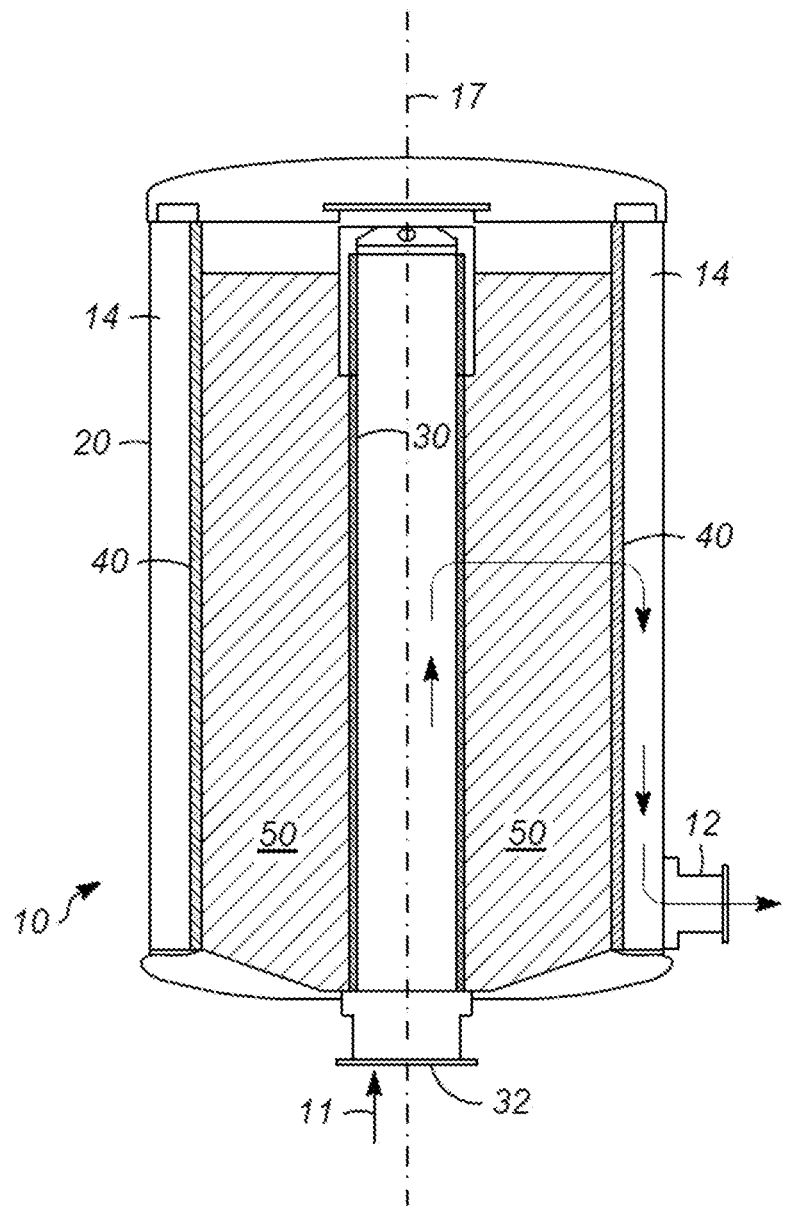
FIG. 1 is a schematic of a single radial flow dehydrogenation reactor.
Figure 2:
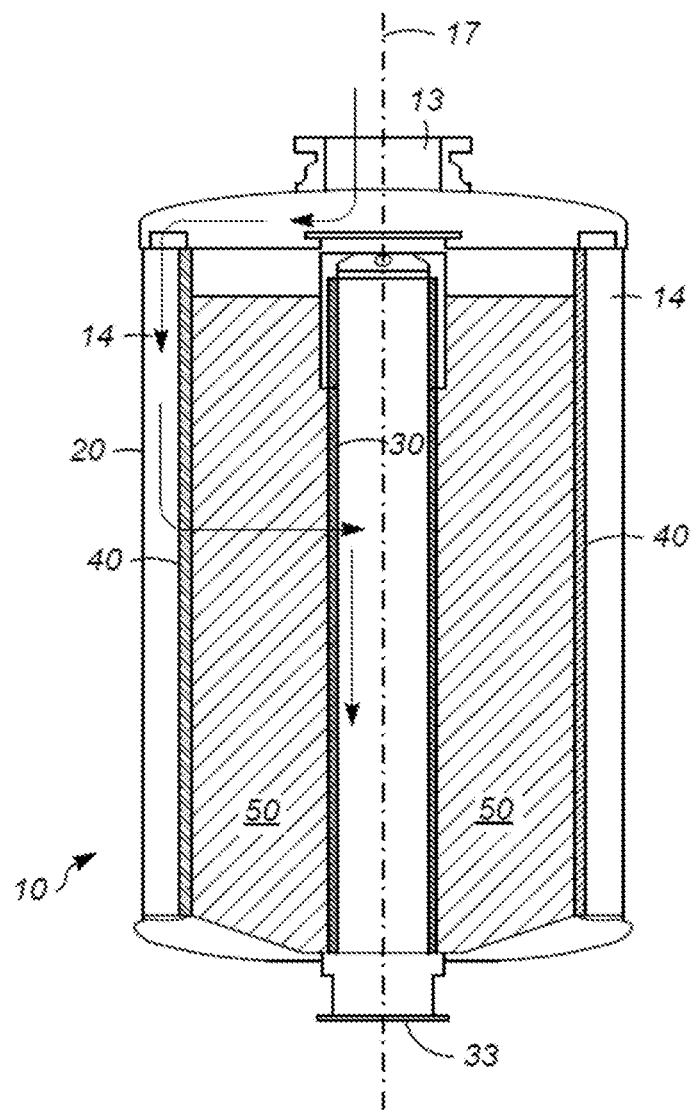
FIG. 2 is a schematic of a single radial reversed flow dehydrogenation reactor.

It has been surprisingly discovered that it is possible to significantly reduce the pressure drop through the catalyst bed and reactor screens by coupling large pill, low density dehydrogenation catalysts and large slot width screens compared to conventional screen and catalyst size combinations.

The larger catalyst pills have a lower apparent bulk density (ABD) compared to conventional catalyst pills in order to improve mass transfer properties for the dehydrogenation reaction and for the coke burn reaction during catalyst regeneration. Surprisingly, the larger catalyst pills with lower ABD had higher piece crush strength (PCS) compared to the conventional catalyst pills. The higher PCS results in less pill breakage and less fines, allowing the use of larger slot width screen in the dehydrogenation reactor.

The dehydrogenation catalyst comprises a Group VIII noble metal component (e.g., platinum, iridium, rhodium, and palladium), a Group IA or IIA metal component, a component selected from the group consisting of tin, germanium, lead, indium, gallium, thallium or mixtures thereof, and a porous inorganic carrier material. The porous inorganic carrier material which confers the catalyst particles the size, shape, strength and mass transport properties, should be relatively refractory to the conditions utilized in the reaction zone. A preferred porous carrier material is alumina carrier material comprising essentially theta alumina. The conventional dehydrogenation catalyst particles are usually spheroidal and have an average particle diameter of about 1.6 mm and an ABD of greater than about 0.6 g/cm$^3$. The conventional inner screens have a slot width of 0.61 mm, while the conventional outer screens have a slot width of 0.48 mm.

The catalyst used in this invention is a large pill, low density catalyst comprising: a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof; and a support forming a spherical catalyst particle with a median diameter between 1.6 mm and 3.0 mm, an average pore diameter between 200 to 350 Angstroms, and an apparent bulk density between 0.6 and 0.3 g/cc, wherein the catalyst particle has an effective carbon dioxide diffusivity at 10° C. of at least $1.6 \times 10^{-6}$ m$^2$/sec, or has an oxygen effective diffusivity at 480° C. of at least $1.5 \times 10^{-7}$ m$^2$/s, or has both. We have found that the new low density catalyst with large pore volume, large porosity, and large pore diameter offers several advantages, especially in a diffusion limited reaction. Specifically, this combination of properties provides the new catalytic material improved dehydrogenation performance and regeneration (i.e., coke burn). Additionally, the new catalytic material has higher piece crush strength, potentially leading to less fines produced in the reactor. In addition, the new catalytic material offers the possibility of increasing the throughput for the reactor allowing for a higher mass flow through the unit.

One aspect of the invention is a process for dehydrogenation of a hydrocarbon feed. In one embodiment, the process comprises providing a hydrocarbon feed stream comprising at least one paraffin to a dehydrogenation reactor, the reactor comprising a shell containing at least one screen. The feed stream is contacted with a catalyst in the reactor under dehydrogenation conditions, the catalyst having an average pill diameter in a range of 1.6 mm to 3.0 mm, and wherein a screen slot width of the at least one screen is in a range of about 30% to about 60% of the pill diameter. The effluent stream comprising at least one olefin is removed from the reactor.

In some embodiments, the screen slot width is in the range of about 30% to about 40% of the average pill diameter. In some embodiments, the screen slot width is in the range of about 40% to about 50% of the average pill diameter. In some embodiments, the relative screen delta pressure drop in the screen slot width range is decreased by about 35-55% compared to a process having screen slot width in the range of about 30% to about 40% of the average pill diameter. In some embodiments, the screen slot width is in the range of about 50% to about 60% of the average pill diameter. In some embodiments, the relative screen delta pressure drop in the screen slot width range is decreased by about 50 to 65%% compared to a process having screen slot width in the range of about 30% to about 40% of the average pill diameter.

In some embodiments, the relative delta pressure in the catalyst bed is decreased by at least 15% compared to a process using a catalyst having an average pill diameter of less than 1.6 mm. In some embodiments, the relative delta pressure in the catalyst bed is decreased by at least 30% compared to a process using a catalyst having an average pill diameter of less than 1.6 mm. In some embodiments, the relative delta pressure in the catalyst bed is decreased by at least 45% compared to a process using a catalyst having an average pill diameter of less than 1.6 mm. In some embodiments, the relative delta pressure in the catalyst bed is decreased by at least 60% compared to a process using a catalyst having an average pill diameter of less than 1.6 mm.

In some embodiments, the catalyst has a higher piece crush strength than a catalyst having an average pill diameter of less than 1.6 mm.

In some embodiments, the catalyst has a lower apparent bulk density than a catalyst having an average pill diameter of less than 1.6 mm.

In some embodiments, the process further comprises at least one of: sensing at least one parameter of the process and generating a signal or data from the sensing; generating and transmitting a signal; or generating and transmitting data.

Another aspect of the invention is a process for dehydrogenation of a hydrocarbon feed. In one embodiment, the process comprises providing a hydrocarbon feed stream comprising at least one paraffin to a dehydrogenation reactor, the reactor comprising a shell containing at least one screen. The feed stream is contacted with a catalyst in the reactor under dehydrogenation conditions, the catalyst having an average pill diameter in a range of 1.6 mm to 3.0 mm, and wherein a screen slot width of the at least one screen is in a range of about 30% to about 60% of the pill diameter. The effluent stream comprising at least one olefin is removed from the reactor. The relative delta pressure in the catalyst bed is decreased by at least 15% compared to a process using a catalyst having an average pill diameter of less than 1.6 mm.

In some embodiments, the relative delta pressure in the catalyst bed is decreased by at least 30% compared to a process using a catalyst having an average pill diameter of less than 1.6 mm. In some embodiments, the relative delta pressure in the catalyst bed is decreased by at least 45% compared to a process using a catalyst having an average pill diameter of less than 1.6 mm. In some embodiments, the relative delta pressure in the catalyst bed is decreased by at least 60% compared to a process using a catalyst having an average pill diameter of less than 1.6 mm.

In some embodiments, the screen slot width is in the range of about 30% to about 40% of the average pill diameter. In some embodiments, the screen slot width is in the range of about 40% to about 50% of the average pill diameter. In some embodiments, the screen slot width is in the range of about 50% to about 60% of the average pill diameter.

In some embodiments, the relative delta pressure in the catalyst bed is decreased by at least 30% compared to a process using a catalyst having an average pill diameter of less than 1.6 mm.

In some embodiments, the relative screen delta pressure drop in the screen slot width range is decreased by about 35-55% compared to a process having screen slot width in the range of about 30% to about 40% of the average pill diameter.

In some embodiments, the relative screen delta pressure drop in the screen slot width range is decreased by about 50 to 65% compared to a process having screen slot width in the range of about 30% to about 40% of the average pill diameter.

In some embodiments, the catalyst has a higher piece crush strength than a catalyst having an average pill diameter of less than 1.6 mm, or the catalyst has a lower apparent bulk density than a catalyst having an average pill diameter of less than 1.6 mm, or both.

Another aspect of the invention is a dehydrogenation reactor. In one embodiment, the reactor comprises a shell having a feed inlet and an effluent outlet, the shell containing a pair of screens; and a catalyst having an average pill diameter in a range of 1.6 mm to 3.0 mm, and wherein a screen slot width of the pair of screens is in a range of about 30% to about 60% of the pill diameter, wherein the catalyst has a higher piece crush strength than a catalyst having an average pill diameter of less than 1.6 mm, the catalyst positioned between the pair of screens.

In some embodiments, the catalyst has a higher piece crush strength than a catalyst having an average pill diameter of less than 1.6 mm, or wherein the catalyst has a lower apparent bulk density than a catalyst having an average pill diameter of less than 1.6 mm, or both.

The dehydrogenation of paraffinic hydrocarbons is well known to those skilled in the art of hydrocarbon processing. Dehydrogenatable hydrocarbons are contacted with the catalytic composition described above in a dehydrogenation zone maintained at dehydrogenation conditions. This contacting may be accomplished in a fixed catalyst bed system, a moving catalyst bed system, a fluidized bed system, etc., or in a batch-type operation. The dehydrogenation zone may comprise one or more separate reaction zones with heating means therebetween to ensure that the desired reaction temperature can be maintained at the entrance to each reaction zone. The hydrocarbon may be contacted with the catalyst bed in either upward, downward, or radial flow fashion. Radial flow of the hydrocarbon through the catalyst bed is preferred for commercial scale reactors. The hydrocarbon may be in the liquid phase, a mixed vapor-liquid phase, or the vapor phase when it contacts the catalyst.

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of $C_2$-$C_6$ paraffins, primarily propane and butanes, to monoolefins.

Dehydrogenation conditions include a temperature of from about 400° to about 900° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while, or after being passed to the dehydrogenation zone. The diluent material may be hydrogen, steam, methane, ethane, carbon dioxide, nitrogen, argon, and the like or a mixture thereof. Hydrogen and steam are the preferred diluents. Ordinarily, when hydrogen or steam is utilized as the diluent, it is utilized in amounts sufficient to ensure a diluent-to-hydrocarbon mole ratio of about 0.1:1 to about 40:1, with best results being obtained when the mole ratio range is about 0.4:1 to about 10:1. The diluent stream passed to the dehydrogenation zone will typically be recycled diluent separated from the effluent from the dehydrogenation zone in a separation zone.

A combination of diluents, such as steam with hydrogen, may be employed. When hydrogen is the primary diluent water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins have from 6 to 30 or more carbon atoms.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. Some processes have been developed which utilize a two-catalyst system with distinct beds or reactors of dehydrogenation or selective oxidation catalysts. The purpose of the selective oxidation catalysts is to selectively oxidize the hydrogen produced as a result of the dehydrogenation reaction with oxygen that had been added to the oxidation zone to generate heat internally in the process. The heat generated typically is sufficient to cause the reaction mixture to reach desired dehydrogenation temperatures for the next dehydrogenation step. The instant process may be accomplished in this previously mentioned system. If such a process is employed, the instant catalyst would comprise at least the dehydrogenation catalyst with another specific catalyst being used to accomplish the oxidation reaction.

The selective oxidation step, if utilized, uses the hydrogen which has been produced in the dehydrogenation step of the process to supply heat to the next dehydrogenation reaction section. To accomplish this, an oxygen-containing gas is first introduced into the reactor, preferably at a point adjacent to the selective oxidative catalyst section. The oxygen in the oxygen-containing gas is necessary to oxidize the hydrogen contained in the reaction stream. Examples of oxygen-containing gases which may be utilized to effect the selective oxidation of the hydrogen which is present will include air, oxygen, or air or oxygen diluted with other gases such as steam, carbon dioxide and inert gases such as nitrogen, argon, helium, etc. The amount of oxygen which is introduced to contact the process stream may range from about 0.01:1 to about 2:1 moles of oxygen per mole of hydrogen contained in the process stream at the point where oxygen is added to the process stream. In the selective oxidation reaction, the process stream which comprises unreacted dehydrogenatable hydrocarbon, dehydrogenated hydrocarbon, and hydrogen is reacted with oxygen in the presence of the selective steam oxidation/dehydrogenation catalyst whereby hydrogen is selectively oxidized to produce water and heat energy with very little of the oxygen reacting with the hydrocarbons.

The selective steam oxidation/dehydrogenation catalyst may be one that is useful for the selective oxidation of hydrogen in the presence of hydrocarbons. An example of such a catalyst is disclosed in U.S. Pat. No. 4,418,237. Alternatively, the catalyst used for the selective oxidation step may be identical to the catalyst utilized for the dehydrogenation step. Such catalysts or processes for their use are disclosed in U.S. Pat. Nos. 4,613,715 and 3,670,044.

The oxygen-containing reactant may be added to the instant process in various ways such as by admixing oxygen with a relatively cool hydrocarbon feed stream or with the steam diluent, or it may be added directly to the reactor independently of the feed hydrocarbons or the steam diluent. In addition, the oxygen-containing reactant can be added at one or more points in the reactor in such a fashion as to minimize local concentrations of oxygen relative to hydrogen in order to distribute the beneficial temperature rise produced by the selective hydrogen oxidation over the entire length of the reaction zone. The use of multiple injection points minimizes the opportunity for local build-up of the concentration of oxygen relative to the amount of hydrogen, thereby minimizing the opportunity for undesired reaction of the oxygen-containing gas with either feed or product hydrocarbons.

EXAMPLE

Figure 3:
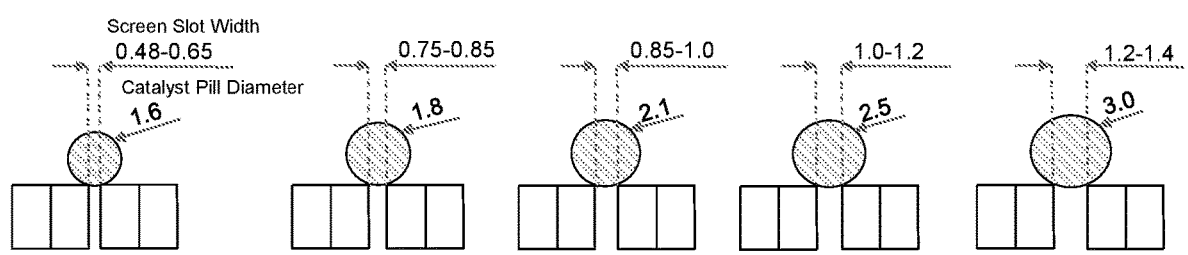
FIG. 3 shows a simplified schematic of outer screen slot width openings and spherical dehydrogenation catalyst pills.

Combinations of large pill dehydrogenation catalysts with lower apparent bulk density and large piece crush strength, and corresponding large inner and outer screen slot widths are evaluated for a reduction in pressure drop across the catalyst bed and reactor screens, and are compared to conventional screen slot width opening and catalyst pill size combination. FIG. 3 shows the ranges of inner and outer screen slot widths with the corresponding catalyst pill diameters. Table 1 shows the ranges of inner and outer screen slot widths with the corresponding catalyst pill diameters, the relative bed delta pressure decrease and the screen slot width relative delta pressure decrease. In following the method of this invention, the bed pressure drop and screen slot width pressure drop by at least 15% compared to the base case.

TABLE 1

Catalyst pill diameters and corresponding inner and outer screen slot width openings and catalyst bed relative % dP decrease and screen slot width relative % dP decrease versus base case.

| Nr. | Catalyst Pill Diameter (mm) | Catalyst Pill Diameter (in) | Inner Screen Slot Width Range (mm) | Outer Screen Slot Width Range (mm) | Reactor Bed delta P (lb/in$^2$) | Catalyst Bed Relative % dP Decrease | Screen Slot Width Range Relative % dP Decrease |
|---|---|---|---|---|---|---|---|
| 1 | 1.6 | 0.063 | 0.6-0.75 | 0.48-0.65 | 0.3991-0.449 | | |
| 2 | 1.8 | 0.0709 | 0.85-1.0 | 0.75-0.85 | 0.3281-0.3771 | 16%-18% | 35%-55% |
| 3 | 2.1 | 0.0827 | 1.0-1.2 | 0.85-1.0 | 0.2576-0.3024 | 33%-35% | 40%-65% |
| 4 | 2.5 | 0.0984 | 1.2-1.4 | 1.0-1.2 | 0.1966-0.2365 | 47%-51% | 50%-75% |
| 5 | 3 | 0.1181 | 1.4-1.7 | 1.2-1.4 | 0.1497-0.1846 | 59%-62% | 65%-80% |

Specific Embodiments

While the following is described in conjunction with specific embodiments, it will be understood that this description is intended to illustrate and not limit the scope of the preceding description and the appended claims.

A first embodiment of the invention is a process for dehydrogenation of a hydrocarbon feed comprising providing a hydrocarbon feed stream comprising at least one paraffin to a dehydrogenation reactor, the reactor comprising a shell containing at least one screen; contacting the feed stream with a catalyst in the reactor under dehydrogenation conditions, the catalyst having an average pill diameter in a range of 1.6 mm to 3.0 mm, and wherein a screen slot width of the at least one screen is in a range of about 30% to about 60% of the pill diameter; and removing an effluent stream comprising at least one olefin from the reactor. An embodiment of the invention is one, any or all of prior embodiments in this paragraph up through the first embodiment in this paragraph wherein the slot width is in the range of about 30% to about 40% of the average pill diameter. An embodiment of the invention is one, any or all of prior embodiments in this paragraph up through the first embodiment in this paragraph wherein the screen slot width is in the range of about 40% to about 50% of the average pill diameter. An embodiment of the invention is one, any or all of prior embodiments in this paragraph up through the first embodiment in this paragraph wherein the relative screen delta pressure drop in the screen slot width range is decreased by about 35-55% compared to a process having screen slot width in the range of about 30% to about 40% of the average pill diameter. An embodiment of the invention is one, any or all of prior embodiments in this paragraph up through the first embodiment in this paragraph wherein the screen slot width is in the range of about 50% to about 60% of the average pill diameter. An embodiment of the invention is one, any or all of prior embodiments in this paragraph up through the first embodiment in this paragraph wherein the relative screen delta pressure drop in the screen slot width range is decreased by about 50 to 65% compared to a process having screen slot width in the range of about 30% to about 40% of the average pill diameter. An embodiment of the invention is one, any or all of prior embodiments in this paragraph up through the first embodiment in this paragraph wherein the relative delta pressure in the catalyst bed is decreased by at least 15% compared to a process using a catalyst having an average pill diameter of less than 1.6 mm. An embodiment of the invention is one, any or all of prior embodiments in this paragraph up through the first embodiment in this paragraph wherein the relative delta pressure in the catalyst bed is decreased by at least 30% compared to a process using a catalyst having an average pill diameter of less than 1.6 mm. An embodiment of the invention is one, any or all of prior embodiments in this paragraph up through the first embodiment in this paragraph wherein the relative delta pressure in the catalyst bed is decreased by at least 45% compared to a process using a catalyst having an average pill diameter of less than 1.6 mm. An embodiment of the invention is one, any or all of prior embodiments in this paragraph up through the first embodiment in this paragraph wherein the relative delta pressure in the catalyst bed is decreased by at least 60% compared to a process using a catalyst having an average pill diameter of less than 1.6 mm. An embodiment of the invention is one, any or all of prior embodiments in this paragraph up through the first embodiment in this paragraph wherein the catalyst has a higher piece crush strength than a catalyst having an average pill diameter of less than 1.6 mm. An embodiment of the invention is one, any or all of prior embodiments in this paragraph up through the first embodiment in this paragraph wherein the catalyst has a lower apparent bulk density than a catalyst having an average pill diameter of less than 1.6 mm. An embodiment of the invention is one, any or all of prior embodiments in this paragraph up through the first embodiment in this paragraph, further comprising at least one of sensing at least one parameter of the process and generating a signal or data from the sensing; generating and transmitting a signal; or generating and transmitting data.

A second embodiment of the invention is a process for dehydrogenation of a hydrocarbon feed comprising providing a hydrocarbon feed stream comprising at least one paraffin to a dehydrogenation reactor, the reactor comprising a shell containing at least one screen; contacting the feed stream with a catalyst in the reactor under dehydrogenation conditions, the catalyst having an average pill diameter in a range of 1.6 mm to 3.0 mm, and wherein a screen slot width of the at least one screen is in a range of about 30% to about 60% of the pill diameter; removing an effluent stream comprising at least one olefin from the reactor; wherein the relative delta pressure in the catalyst bed is decreased by at least 15% compared to a process using a catalyst having an average pill diameter of less than 1.6 mm. An embodiment of the invention is one, any or all of prior embodiments in this paragraph up through the second embodiment in this paragraph wherein the relative delta pressure in the catalyst bed is decreased by at least 30% compared to a process using a catalyst having an average pill diameter of less than 1.6 mm. An embodiment of the invention is one, any or all of prior embodiments in this paragraph up through the second embodiment in this paragraph wherein the relative delta pressure in the catalyst bed is decreased by at least 60% compared to a process using a catalyst having an average pill diameter of less than 1.6 mm. An embodiment of the invention is one, any or all of prior embodiments in this paragraph up through the second embodiment in this paragraph wherein the relative screen delta pressure drop in the screen slot width range is decreased by about 35-55% compared to a process having screen slot width in the range of about 30% to about 40% of the average pill diameter. An embodiment of the invention is one, any or all of prior embodiments in this paragraph up through the second embodiment in this paragraph wherein the relative screen delta pressure drop in the screen slot width range is decreased by about 50 to 65% compared to a process having screen slot width in the range of about 30% to about 40% of the average pill diameter. An embodiment of the invention is one, any or all of prior embodiments in this paragraph up through the second embodiment in this paragraph wherein the catalyst has a higher piece crush strength than a catalyst having an average pill diameter of less than 1.6 mm, or wherein the catalyst has a lower apparent bulk density than a catalyst having an average pill diameter of less than 1.6 mm, or both.

A third embodiment of the invention is an apparatus comprising a shell having a feed inlet and an effluent outlet, the shell containing a pair of screens; and a catalyst having an average pill diameter in a range of 1.6 mm to 3.0 mm, and wherein a screen slot width of the pair of screens is in a range of about 30% to about 60% of the pill diameter, wherein the catalyst has a higher piece crush strength than a catalyst having an average pill diameter of less than 1.6 mm, or wherein the catalyst has a lower apparent bulk density than a catalyst having an average pill diameter of less than 1.6 mm, or both, the catalyst positioned between the pair of screens.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed is:

1. A process for dehydrogenation of a hydrocarbon feed comprising:
   providing a hydrocarbon feed stream comprising at least one paraffin to a dehydrogenation reactor, the reactor comprising a shell containing at least one screen;
   contacting the feed stream with a catalyst in the reactor under dehydrogenation conditions, the catalyst having an average pill diameter in a range of 1.6 mm to 3.0 mm, and wherein a catalyst-side screen slot width of the at least one screen is in a range of about 30% to about 60% of the pill diameter; and
   removing an effluent stream comprising at least one olefin from the reactor.

2. The process of claim 1 wherein the slot width is in the range of about 30% to about 40% of the average pill diameter.

3. The process of claim 1 wherein the screen slot width is in the range of about 40% to about 50% of the average pill diameter.

4. The process of claim 1 wherein the relative screen delta pressure drop in the screen slot width range is decreased by about 35-55% compared to a process having screen slot width in the range of about 30% to about 40% of the average pill diameter.

5. The process of claim 1 wherein the screen slot width is in the range of about 50% to about 60% of the average pill diameter.

6. The process of claim 1 wherein the relative screen delta pressure drop in the screen slot width range is decreased by about 50 to 65% compared to a process having screen slot width in the range of about 30% to about 40% of the average pill diameter.

7. The process of claim 1 wherein the relative delta pressure in the catalyst bed is decreased by at least 15% compared to a process using a catalyst having an average pill diameter of less than 1.6 mm.

8. The process of claim 1 wherein the relative delta pressure in the catalyst bed is decreased by at least 30% compared to a process using a catalyst having an average pill diameter of less than 1.6 mm.

9. The process of claim 1 wherein the relative delta pressure in the catalyst bed is decreased by at least 45% compared to a process using a catalyst having an average pill diameter of less than 1.6 mm.

10. The process of claim 1 wherein the relative delta pressure in the catalyst bed is decreased by at least 60% compared to a process using a catalyst having an average pill diameter of less than 1.6 mm.

11. The process of claim 1 wherein the catalyst has a higher piece crush strength than a catalyst having an average pill diameter of less than 1.6 mm.

12. The process of claim 1 wherein the catalyst has a lower apparent bulk density than a catalyst having an average pill diameter of less than 1.6 mm.

13. The process of claim 1, further comprising at least one of:
sensing at least one parameter of the process and generating a signal or data from the sensing;
generating and transmitting a signal; or
generating and transmitting data.

14. A process for dehydrogenation of a hydrocarbon feed comprising:
providing a hydrocarbon feed stream comprising at least one paraffin to a dehydrogenation reactor, the reactor comprising a shell containing at least one screen;
contacting the feed stream with a catalyst in the reactor under dehydrogenation conditions, the catalyst having an average pill diameter in a range of 1.6 mm to 3.0 mm, and wherein a catalyst-side screen slot width of the at least one screen is in a range of about 30% to about 60% of the pill diameter;
removing an effluent stream comprising at least one olefin from the reactor;
wherein the relative delta pressure in the catalyst bed is decreased by at least 15% compared to a process using a catalyst having an average pill diameter of less than 1.6 mm.

15. The process of claim 14 wherein the relative delta pressure in the catalyst bed is decreased by at least 30% compared to a process using a catalyst having an average pill diameter of less than 1.6 mm.

16. The process of claim 14 wherein the relative delta pressure in the catalyst bed is decreased by at least 60% compared to a process using a catalyst having an average pill diameter of less than 1.6 mm.

17. The process of claim 14 wherein the relative screen delta pressure drop in the screen slot width range is decreased by about 35-55% compared to a process having screen slot width in the range of about 30% to about 40% of the average pill diameter.

18. The process of claim 14 wherein the relative screen delta pressure drop in the screen slot width range is decreased by about 50 to 65% compared to a process having screen slot width in the range of about 30% to about 40% of the average pill diameter.

19. The process of claim 14 wherein the catalyst has a higher piece crush strength than a catalyst having an average pill diameter of less than 1.6 mm, or wherein the catalyst has a lower apparent bulk density than a catalyst having an average pill diameter of less than 1.6 mm, or both.

20. A dehydrogenation reactor comprising:
a shell having a feed inlet and an effluent outlet, the shell containing a pair of screens; and
a catalyst having an average pill diameter in a range of 1.6 mm to 3.0 mm, and wherein a catalyst-side screen slot width of the pair of screens is in a range of about 30% to about 60% of the pill diameter, wherein the catalyst has a higher piece crush strength than a catalyst having an average pill diameter of less than 1.6 mm, or wherein the catalyst has a lower apparent bulk density than a catalyst having an average pill diameter of less than 1.6 mm, or both, the catalyst positioned between the pair of screens.

* * * * *